United States Patent
Stogniew

(10) Patent No.: US 6,991,800 B2
(45) Date of Patent: Jan. 31, 2006

(54) ANTIFUNGAL PARENTERAL PRODUCTS

(75) Inventor: Martin Stogniew, Blue Bell, PA (US)

(73) Assignee: Vicuron Pharmaceuticals Inc., Fremont, CA (US)

( * ) Notice: Subject to any disclaimer, the term of this patent is extended or adjusted under 35 U.S.C. 154(b) by 51 days.

(21) Appl. No.: 10/172,678

(22) Filed: Jun. 13, 2002

(65) Prior Publication Data

US 2004/0223997 A1    Nov. 11, 2004

(51) Int. Cl.
A61K 9/08       (2006.01)
A01N 25/04      (2006.01)

(52) U.S. Cl. .................. 424/405; 424/400; 514/23; 514/359

(58) Field of Classification Search ............ 424/400, 424/405; 514/23, 359
See application file for complete search history.

(56) References Cited

U.S. PATENT DOCUMENTS

| | | |
|---|---|---|
| 3,293,482 A | 12/1966 | Wolkstein |
| 3,978,210 A | 8/1976 | Mizuno et al. |
| 4,293,482 A | 10/1981 | Abbott et al. |
| 4,293,483 A | 10/1981 | Debono |
| 4,293,489 A | 10/1981 | Debono |
| 4,299,763 A | 11/1981 | Abbott et al. |
| 4,304,716 A | 12/1981 | Abbott et al. |
| 4,320,052 A | 3/1982 | Abbott et al. |
| 4,348,384 A | 9/1982 | Horikoshi et al. |
| 4,876,241 A | 10/1989 | Feldman et al. |
| 4,927,831 A | 5/1990 | Malamas |
| 5,141,674 A | 8/1992 | Leigh |
| 5,166,135 A | 11/1992 | Schmatz |
| 5,198,421 A | 3/1993 | Chen et al. |
| 5,202,309 A | 4/1993 | Schwartz et al. |
| 5,376,634 A | 12/1994 | Iwamoto et al. |
| 5,541,160 A | 7/1996 | Balkovec et al. |
| 5,573,936 A | 11/1996 | Kreuzman et al. |
| 5,618,787 A | 4/1997 | Jamison et al. |
| 5,629,289 A | 5/1997 | Rodriguez |
| 5,629,290 A | 5/1997 | LaGrandeur et al. |
| 5,646,111 A | 7/1997 | Borromeo et al. |
| 5,652,213 A | 7/1997 | Jamison et al. |
| 5,693,611 A | 12/1997 | Henle et al. |
| 5,696,084 A | 12/1997 | Lartey et al. |
| 5,741,775 A | 4/1998 | Balkovec et al. |
| 5,786,325 A | 7/1998 | Borromeo et al. |
| 5,932,543 A | 8/1999 | Burkhardt et al. |
| 5,952,008 A | 9/1999 | Backstrom et al. |
| 5,965,525 A | 10/1999 | Burkhardt et al. |
| 5,972,996 A | 10/1999 | Nielsen-Kahn et al. |
| 5,985,309 A | 11/1999 | Edwards et al. |
| 5,993,805 A | 11/1999 | Sutton et al. |
| 6,001,336 A | 12/1999 | Gordon |
| 6,043,341 A | 3/2000 | Udodong et al. |
| 6,153,224 A | 11/2000 | Staniforth |
| 6,258,821 B1 | 7/2001 | Stogniew et al. |
| 6,267,958 B1 | 7/2001 | Andya et al. |
| 6,284,277 B1 | 9/2001 | Bouloumie et al. |
| 6,284,282 B1 | 9/2001 | Maa et al. |
| 6,309,623 B1 | 10/2001 | Weers et al. |
| 6,323,176 B1 | 11/2001 | Jamison et al. |
| 6,384,013 B1 | 5/2002 | Burkhardt et al. |
| 6,433,040 B1 | 8/2002 | Dellamary et al. |
| 6,451,349 B1 | 9/2002 | Robinson et al. |
| 6,475,523 B1 | 11/2002 | Staniforth |
| 6,506,726 B1 | 1/2003 | Dobbins et al. |
| 6,565,885 B1 | 5/2003 | Tarara et al. |
| 6,590,073 B2 | 7/2003 | Dalder et al. |
| 6,638,495 B2 | 10/2003 | Weers et al. |
| 6,653,281 B1 | 11/2003 | Borromeo et al. |
| 6,660,843 B1 | 12/2003 | Feige et al. |
| 6,670,324 B2 | 12/2003 | Jamison et al. |
| 6,689,390 B2 | 2/2004 | Bernstein et al. |
| 6,709,650 B1 | 3/2004 | Sutton et al. |
| 6,743,777 B1 | 6/2004 | Burkhardt et al. |
| 2002/0151474 A1 | 10/2002 | Schweir et al. |
| 2002/0160942 A1 | 10/2002 | Larew et al. |
| 2002/0161176 A1 | 10/2002 | Dalder et al. |
| 2003/0039667 A1 | 2/2003 | Jira et al. |
| 2003/0054981 A1 | 3/2003 | Milton et al. |
| 2003/0104048 A1 | 6/2003 | Patel et al. |
| 2003/0220236 A1 | 11/2003 | Burkhardt et al. |

FOREIGN PATENT DOCUMENTS

| | | |
|---|---|---|
| CA | 2043762 | 12/1991 |
| DE | 28 03 851 A1 | 8/1979 |
| EP | 0 031 221 | 7/1981 |
| EP | 0 032 009 A1 | 7/1981 |
| EP | 0 359 529 | 3/1990 |
| EP | 0 365 324 A1 | 4/1990 |

(Continued)

OTHER PUBLICATIONS

Avis, K. E. (1990). "Parenteral Preparations" Chapter 84 In *Remington Pharmaceutical Sciences*. 18th edition, Mack Publishing Company p. 1545-1569.

(Continued)

Primary Examiner—Leon B. Lankford, Jr.
Assistant Examiner—Ruth A. Davis
(74) Attorney, Agent, or Firm—Morrison & Foerster LLP

(57) ABSTRACT

Parenteral pharmaceutical formulations containing an echinocandin antifungal compound and an aqueous solvent are provided, wherein the formulation includes ethanol, for example about 20% w/v ethanol. The parenteral pharmaceutical formulation may further include one or more additives, such as a stabilizing agent, buffer or tonicity agent. The parenteral pharmaceutical formulations are useful in extending the shelf life and improving the solubility of the echinocandin antifungal compound.

48 Claims, No Drawings

FOREIGN PATENT DOCUMENTS

| | | |
|---|---|---|
| EP | 0 365 324 B1 | 4/1990 |
| EP | 0 447 186 | 9/1991 |
| EP | 0 448 343 A2 | 9/1991 |
| EP | 0 448 343 A3 | 9/1991 |
| EP | 0 448 353 | 9/1991 |
| EP | 0 448 354 A2 | 9/1991 |
| EP | 0 448 354 A3 | 9/1991 |
| EP | 0 448 355 A2 | 9/1991 |
| EP | 0 448 355 A3 | 9/1991 |
| EP | 0 448 356 A2 | 9/1991 |
| EP | 0 448 356 A3 | 9/1991 |
| EP | 0 460 882 | 12/1991 |
| EP | 0 462 531 | 12/1991 |
| EP | 0 486 011 A2 | 5/1992 |
| EP | 0 486 011 A3 | 5/1992 |
| EP | 0 503 960 A1 | 9/1992 |
| EP | 0 525 889 A1 | 2/1993 |
| EP | 0 561 639 | 9/1993 |
| EP | 0 589 074 | 3/1994 |
| EP | 0 744 405 | 11/1996 |
| EP | 0 757 058 | 2/1997 |
| EP | 0 931 834 | 7/1999 |
| GB | 2241956 A | 9/1991 |
| GB | 2242194 A | 9/1991 |
| JP | 03 240727 | 10/1991 |
| JP | 05 271097 | 10/1993 |
| JP | 5-271097 A | 10/1993 |
| JP | 06 172205 | 6/1994 |
| JP | 6-172205 A | 6/1994 |
| WO | WO 94/25084 | 11/1994 |
| WO | WO-95/27074 A1 | 10/1995 |
| WO | WO 96/31228 | 10/1996 |
| WO | WO 96/37509 | 11/1996 |
| WO | WO 96/37510 | 11/1996 |
| WO | WO 96/37511 | 11/1996 |
| WO | WO 96/37512 | 11/1996 |
| WO | WO 97/05163 | 2/1997 |
| WO | WO 97/27864 | 8/1997 |
| WO | WO 97/30695 | 8/1997 |
| WO | WO 99/06062 | 2/1999 |
| WO | WO 99/43337 | 9/1999 |
| WO | WO 00/11023 | 3/2000 |
| WO | WO 00/12540 | 3/2000 |
| WO | WO 00/34315 | 6/2000 |
| WO | WO 00/35944 | 6/2000 |
| WO | WO 00/35945 | 6/2000 |
| WO | WO 00/51564 | 9/2000 |
| WO | WO 00/51567 | 9/2000 |
| WO | WO 00/52036 | 9/2000 |
| WO | WO 00/52037 | 9/2000 |
| WO | WO-03/105767 A2 | 12/2003 |
| WO | WO-03/105767 A3 | 12/2003 |

OTHER PUBLICATIONS

Etter, M.C. and Baures, P.W. (1988) "Triphenylphosphine Oxide as a Crystallization Aid," *J. Am. Chem. Soc.* 110:639-640.

Ibrahim, F. S. et al., (1995) "the Effect of pH, sugars and calcium ion concentration on the thermal stability of whey proteins" *Egyptian J. Dairy Sci.* 23:177-178.

Longer, M. A. and Robinson, J. R. (1990). "Trasnsdermal Systems" in Chapter 91 *In Remington Pharmaceutical Sciences.* 18th edition, Mack Publishing Company. p. 1690-1693.

Nail, S. and Gattlin, L. A. (1993). "Freeze Drying Principles and Practice" Chapter 3 *In Pharmaceutical Dosage forms*, 2nd edition . K. E. Avis ed. et al., Marcel Dekker, Inc. NY pp. 163-233.

Nema, S. et al. (1997). "Excipients and Their Use in Injectable Products," *PDA Journal of Pharm. Science and Tech.* 51(4):166-171.

Sclarra, J. J. and Cutie, A. J. (1990). "Aerosols" Chapter 92 *In Remington Pharmaceutical Sciences.* 18th edition, Mack Publishing Company. p. 1694-1712.

Turco, S. J. (1990). "Intravenous Admixtures," Chapter 85 *In Remington Pharmaceutical Sciences.* 18th edition, Mack Publishing Company. p. 1570-1580.

Groll, A.H. et al. (2001). "Pharmacokinetic and Pharmacodynamic Modeling of Anidulafungin (LY303366): Reappraisal of Its Efficacy in Neutropenic Animal Models of Opportunistic Mycoses Using Optimal Plasma Sampling," *Antimicrobial Agents and Chemotherapy* 45910):2845-2855.

International Search Report mailed on Dec. 9, 2003, for PCT Patent Application No. PCT/US03/18754 filed on Jun. 12, 2003, 5 pages.

International Search Report for PCT Application No. PCT/US00/05494 filed Mar. 2, 2000, mailed Jun. 7, 2000, three pages.

International Search Report for PCT Application No. PCT/US00/00508 filed Mar. 2, 2000, mailed Aug. 21, 2000, two pages.

International Search Report for PCT Application No. PCT/US00/05546 filed Mar. 2, 2000, mailed Aug. 11, 2000, three pages.

International Search Report for PCT Application No. PCT/US00/05547 filed Mar. 2, 2000, mailed Jul. 19, 2000, two pages.

Keller-Juslen, C. et al. (1976). "Structure of the Cyclopeptide Antibiotic SL 7810 (=Echinocandin B)," *Tetrahedron Letters* 46:4147-4150.

Turner, W.W. et al. (1996). "Recent Advances in the Medicinal Chemistry of Antifungal Agents," *Current Pharmaceutical Design* 2:209-224.

Debono, M. et al. (1995). "Semisynthetic Chemical Modification of the Antifungal Lipopeptide Echinocandin B (ECB): Structure-Activity Studies of the Lipophilic and geometric Parameters of Polyarylated Acyl Analogs of ECB," *J Med Chem.* 38(17):3271-3281.

ANTIFUNGAL PARENTERAL PRODUCTS

TECHNICAL FIELD

This invention relates to drug formulations, for example, aqueous injectable drug formulations and methods for their manufacture and use.

BACKGROUND OF THE INVENTION

One aspect of the commercial viability of an injectable drug product is long shelf life. A shelf life significantly greater than one year is typically needed. This is because drug products are often stored for long periods, for example, six months to a year or more, until needed. The expiration date of a product begins when the drug is produced, but testing and packaging for shipping often take up some time, for example, months. A shelf life of one to three years or more is very desirable for an injectable drug product. This is especially true for a drug which may be stored for a long period of time, because it is not frequently used, but that is specifically required when indicated.

Another aspect of injectable drug products is reconstitution of the formulation by the medical practitioner. The drug may be delivered in a solid form, often called "drug for injection," which may contain other ingredients, and is reconstituted to a liquid form by the addition of solvent and other components.

A USP (United States Pharmacopeia) requirement for parenteral drug products is that the product be visibly clear before use. A vial of crystal clear liquid is desired. To meet this standard, the number of particulates in the reconstituted liquid product must be kept to a minimum. Particulates represent undissolved drug which is ineffective, and may block capillaries causing serious adverse health effects. A crystal clear drug product requires the solution to have a minimum of minute, undissolved, or non-visible drug particles.

Particulates in an injectable drug product may be caused in part by foaming during reconstitution. Foaming may be caused by the drug itself, or by surfactants other additives used to increase and hasten solubility of the drug. Foaming can prevent small particles from entering the solution to be dissolved, thereby increasing the number of particulates in the reconstituted injectable drug product.

Another aspect of parenteral drug products is the time required to reconstitute an injectable formulation. Reconstitution requires the ability to rapidly redissolve a drug composition to provide a crystal clear solution. In addition, the reconstitution should be rapid after a long storage period of the delivered drug composition, a period which can be, for example, one, two, or three years or more. Some drug compositions as delivered typically cannot achieve a shelf life greater than one year. This is because either the reconstitution time is too long after storage, or the number of particulates in the reconstituted product is too high.

Echinocandin antifungal compounds, and methods for their manufacture and use are described, for example, in PCT WO 00/52037; PCT WO 00/51564; PCT WO 00/34315; PCT WO 00/51567; and U.S. Pat. No. 5,965,525.

There is a need for echinocandin pharmaceutical drug formulations that are useful for parenteral pharmaceutical administration with rapid reconstitution, little forming, and a long shelf life.

SUMMARY OF THE INVENTION

In one aspect, a pharmaceutically acceptable parenteral formulations containing an echinocandin and an aqueous ethanolic solvent is provided, as well as optionally one or more additives, such as propylene glycol, or polyethylene glycol, a buffer, stabilizing agent, tonicity agent, antioxidant or bulking agent. Methods of reconstituting solid compositions containing an echinocandin also are provided.

In one embodiment, pharmaceutically acceptable liquid formulations are provided that include, e.g., about 0.2 to 1.0%, or about 0.1 to 2.0% or about 0.2 to 2.0% w/v anidulafungin. The pharmaceutically acceptable liquid formulations also may include, e.g., about 1.0 to 4.0 mg/mL, or about 1.5 to 3.0 mg/mL anidulafungin.

A pharmaceutically acceptable liquid parenteral formulation for example is provided comprising: anidulafungin and an aqueous solvent such as water or saline, wherein the formulation includes from about 5% w/v ethanol to about 50% w/v ethanol; about 15–30% w/v ethanol; or about 20% w/v ethanol. The formulation may include about 10% to about 40% w/v ethanol and about 0.2 to about 2.0% w/v anidulafungin, or optionally about 15 to about 30% w/v ethanol or optionally 20 percent w/v ethanol. The formulation also may include 10 to about 50 percent w/v propylene glycol or polyethylene glycol, or mixtures thereof.

The formulation further may include a stabilizing agent, such as mannitol, histidine, lysine, glycine, sucrose, fructose, trehalose, lactose or a mixture thereof. The formulation can optionally contain a bulking agent, such as mannitol, glycine, lactose, sucrose, trehalose, dextran, hydroxyethyl starch, ficoll or gelatin. The formulation can optionally contain a solubilizing agent or surfactant, such as cetrimide, docusate sodium, glyceryl monooleate, sodium lauryl sulfate, or sorbitan esters. The solubilizing agent or surfactant may optionally be a polyoxyethylenesorbitan fatty acid ester. Polyoxyethylenesorbitan fatty acid esters are also referred to as polysorbates, e.g., polysorbate 80 (polyoxyethylene sorbitan monooleate, Tween 80), polysorbate 40 and polysorbate 20. Polysorbates, such as polysorbate 80, are commercially available, for example, from Sigma, St. Louis, Mo.

The formulation can optionally comprise a buffer, such as acetates, citrates, tartrates, lactates, succinates, or phosphates. The formulation can optionally contain a tonicity agent, such as glycerin, lactose, mannitol, dextrose, sodium chloride, sodium sulfate or sorbitol. The formulation can optionally contain an antioxidant, such as acetone, sodium bisulfite, bisulfite sodium, butylated hydroxy anisole, butylated hydroxy toluene, cysteine, cysteinate HCl, dithionite sodium, gentisic acid, gentisic acid ethanolamine, glutamate monosodium, formaldehyde sulfoxylate sodium, metabisulfite potassium, metabisulfite sodium, monothioglycerol, propyl gallate, sulfite sodium, thioglycolate sodium, or ascorbic acid.

A pharmaceutically acceptable parenteral formulation is also provided for example comprising: anidulafungin and an aqueous solvent, such as water or saline, wherein the formulation includes:
about 5–30% w/v ethanol;
about 0.1–2.0% w/v anidulafungin;
about 0.1–1.0% w/v of a stabilizing agent, such as fructose;
about 0.1–10% w/v of a bulking agent, such as mannitol;
about 0.01–5% w/v of a buffer, such as tartaric acid; and
about 0.1–5.0% w/v of a solubilizing agent, such as polysorbate 80.

The formulation may optionally include about 2–50% w/v polyethylene glycol and/or propylene glycol.

A pharmaceutically acceptable parenteral formulation is also provided comprising: anidulafungin and an aqueous solvent, such as water or saline and ethanol, wherein the anidulafungin is stored in solid form for greater than 6, 9, 12, 15 or 18 months prior to forming the formulation, and wherein the formulation is suitable for use as a parenteral formulation.

A formulation is "suitable for use as a parenteral formulation" if it is in a pharmaceutically acceptable form for parenteral administration. Thus, for example, for a liquid parenteral formulation, the particle content is sufficiently low, and the material is sufficiently sterile such that it is useful for parenteral administration. To be suitable for parenteral administration, the formulation is visibly clear, and the number of particles in the reconstituted liquid product is kept to a minimum. For example, less than 6,000 10 μm particles should be present in a volume of 10 mL solvent that includes 35 mg of anidulafungin. For example, when the drug is freeze dried and stored, for example, for 9 months, 12 months, 18 months or 24 months, and then reconstituted by dissolving 35 mg of drug and optionally other additives in 10 ml of aqueous ethanolic solvent, there are preferably less than 10,000, less than 6,000, less than 3,000, less than 1,000, or less than 400 10 μm particles. There are, for example, less than 1000, less than 600, or less than 200 25 μm particles in the 10 mL volume.

Liquid parenteral formulations formed from drug stored over long time periods can become no longer suitable for parenteral administration, because of particles in the reconstituted formulations. Using the methods disclosed herein, liquid formulations are formed which are suitable for parenteral administration, even when formed from drug stored over long time periods. This can extend the shelf life of the drug. Moreover, using the ethanolic solutions for reconstitution results in more rapid dissolution of the drug.

Also provided is a method of preparing a parenteral pharmaceutical formulation, comprising combining a solid composition comprising anidulafungin and an ethanolic aqueous solvent, such as water, to substantially dissolve the anidulafungin and produce an aqueous formulation including about 5 to about 50% w/v ethanol, optionally 10 to about 30 percent w/v ethanol, wherein the formulation is optionally shaken until the mixture is substantially clear. The method optionally comprises forming the solid composition containing anidulafungin by lyophilizing an aqueous solution of anidulafungin and optionally an additive such as polyethylene glycol or propylene glycol. The solid composition can optionally contain a stabilizing agent, a buffer, a tonicity agent or an antioxidant.

The method optionally comprises preparing a solid composition comprising anidulafungin produced for pharmaceutical use and stored for more than one year before combining with an ethanol water solvent, and wherein the combining step produces a formulation suitable for use as a pharmaceutically acceptable parenteral formulation.

Also provided here is a kit for use in delivery of a pharmaceutically acceptable parenteral pharmaceutical formulation, comprising: a vial containing a pharmaceutically acceptable solid formulation comprising anidulafungin; and a vial comprising a pharmaceutically acceptable aqueous solution of about 10 to 30% w/v ethanol. The kit can optionally contain an additive, such as polyethylene glycol, propylene glycol, a stabilizing agent, a buffer, a tonicity agent and/or an antioxidant. The kit can optionally contain a vial containing a solid formulation comprising 25 to 200 mg of anidulafungin and a second vial containing 5 to 60 milliliters of aqueous solution comprising about 10 to 30% w/v ethanol.

Also provided are pharmaceutically acceptable parenteral formulations including anidulafungin and an aqueous solvent, wherein the anidulafungin is stored for greater than 6, 9, 12, 15, or 18 months before formation of the liquid formulation, and wherein the formulation is suitable for administration as a parenteral formulation.

Further provided are methods of preparing a parenteral formulation, comprising combining a solid formulation comprising anidulafungin with a solvent in an effective amount to dissolve the anidulafungin rapidly, for example in 400 seconds or less, in 200 seconds or less, in 100 seconds or less, or in 60 seconds or less, for example by shaking or swirling, to produce a pharmaceutically acceptable parenteral formulation. The anidulafungin may be a formulation produced for pharmaceutical use and stored, for example for more than one year, or two years, prior to combining with the solvent. The concentration of the anidulafungin is, for example, about 1.5 to 3 mg/mL, or about 1.5 to 5 mg/mL.

DETAILED DESCRIPTION OF THE INVENTION

Provided are pharmaceutically acceptable formulations comprising an echinocandin, such as anidulafungin.

Echinocandins

Echinocandin-type compounds have been shown to exhibit antifungal and antiparasitic activity, such as inhibition of growth of various infectious fungi including *Candida* spp. (i.e., *C Albicans, C Parapsilosis, C Krusei, C Glabrata, C Tropicalis*, or *C Lusitaniaw*); *Torulopus* spp. (i.e., *T Glabrata*); *Aspergillus* spp. (i.e., *A. Fumigalus*), *Histoplasma* spp. (i.e., *H. Capsulatum*); *Cryptococcus* spp. (i.e., *C. Neoformans*); *Blastomyces* spp. (i.e., *B. Dermatilidis*); *Fusarium* spp.; *Trichophyton* spp., *Pseudallescheria boydii, Coccidioides immits*, and *Sporothrix schenckii*, etc. PCT WO 00/51564.

Compounds of this type also have been shown to inhibit the growth of certain organisms primarily responsible for opportunistic infections in immunosuppressed individuals, such as growth inhibition of *Pneumocystis carinii*. Other protozoans that are inhibited by echinocandin-type compounds include *Plasmodium* spp., *Leishmania* spp., *Trypanosoma* spp., *Cryptosporidium* spp., *Isospora* spp., *Cyclospora* spp., *Trichomnas* spp., and *Microsporidiosis* spp., etc. PCT WO 00/51564.

Consequently, the formulations of the present invention are useful in the treatment of, e.g., systemic fungal infections or fungal skin infections. Accordingly, the processes and formulations of the present invention may be used in the manufacture of a medicament for the therapeutic applications described herein. For example, fungal activity (preferably, *Candida albicans* or *Aspergillus fumigatis* activity) or parasitic activity may be inhibited by contacting a pharmaceutical formulation prepared by the present invention with a fungus or parasite, respectively. The term "contacting" includes a union or junction, or apparent touching or mutual tangency of a compound of the invention with a parasite or fungus. The term does not imply any further limitations to the process, such as by mechanism of inhibition. The methods are defined to encompass the inhibition of parasitic and fungal activity by the action of the compounds and their inherent antiparasitic and antifungal properties.

A method for treating a fungal infection which comprises administering an effective amount of a pharmaceutical formulation of the present invention to a host in need of such treatment is also provided. The method includes treating a *Candida albicans* or *Aspergillus fumigatis* infection. The term "effective amount" refers to an amount of active compound which is capable of inhibiting fungal activity. The dose administered will vary depending on such factors as the nature and severity of the infection, the age and general health of the host and the tolerance of the host to the antifungal agent. The particular dose regimen likewise may vary according to these factors. The drug may be given in a single daily dose or in multiple doses during the day. The regimen may last for example, for 2–3 days, for 14–30 days, or longer. An exemplary daily dose (administered in single or divided doses) contains a dosage level between about 0.01 mg/kg to 100 mg/kg of body weight of an active compound. Further exemplary daily doses are about 0.1 mg/kg to 60 mg/kg or about 0.1 mg/kg to 40 mg/kg, or about 0.7 to 3 mg/kg per day. Further exemplary daily doses are about 5 to 500 mg/day or about 50 to 200 mg per day.

Anidulafungin (1-[(4R,5R)-4,5-Dihydroxy-N(2)-[[4"-(pentyloxy)[1,1':4',1"-terphenyl]-4-yl]carbonyl]-L-ornithine]echinocandin B) is an echinocandin that can be semi-synthetically derived from a natural product. The synthesis of anidulafungin is described in U.S. Pat. No. 5,965,525.

Like other echinocandins, anidulafungin has a low water solubility of less than 0.1 mg/ml. Because of the low solubility, formulations have been described that add a surfactant to an aqueous solution, however this can hinder freeze drying (WO 00/51564).

It has been found in the past to be difficult to prepare a formulation of anidulafungin in water which meets the strict USP requirements for purity and clarity of injectable formulations, even when such concentrations are well below the solubility limit in the presence of surfactant species.

The structure of anidulafungin is provided below

Solid Compositions

Solid pharmaceutical compositions containing an echinocandin are provided that can be formulated for administration to a patient in need thereof. Such solid compositions may be reconstituted in an aqueous ethanolic solvent to provide a liquid product, which may be administered to a patient by parenteral means, including subcutaneous, intravenous, bolus injection, intramuscular, or intraarterial injection, or alternatively by oral, topical, transdermal, or mucosal administration.

Solid compositions may have crystalline and amorphous components. A solid composition of an echinocandin may be prepared by lyophilizing (freeze drying) a volume of a solution which contains a known concentration of the echinocandin.

A solid composition comprising anidulafungin can be formed by lyophilizing a solution of anidulafungin, such as an aqueous solution of anidulafungin and optionally one or more additives, such as propylene glycol, or polyethylene glycol, a buffer, stabilizing agent, tonicity agent, antioxidant or bulking agent.

The polyethylene glycol may have, for example, a molecular weight of 400 to about 1500, optionally, 600 to about 1000, often 1000. The addition of polyethylene glycol or propylene glycol optimizes the reconstitution of the lyophilization formulation in an aqueous solvent containing ethanol by providing enhanced solubility. The amount of polyethylene glycol or propylene glycol is, for example, an amount effective to produce the desired concentrations after addition of an aqueous solvent to form a parenteral formulation as discussed herein. In the solid composition, for example, a 50 mg dose of anidulafungin may contain 1.5 grams of PEG.

Solid formulations may optionally contain a stabilizing agent. The solid formulations may contain a stabilizing reagent at a concentration of 5 to 80% w/w, generally 7.6 to 11.5% w/w, or 9.5% w/w. The term "stabilizing agent" refers to a pharmaceutically acceptable excipient that may enhance the chemical or physical stability of the active ingredient in

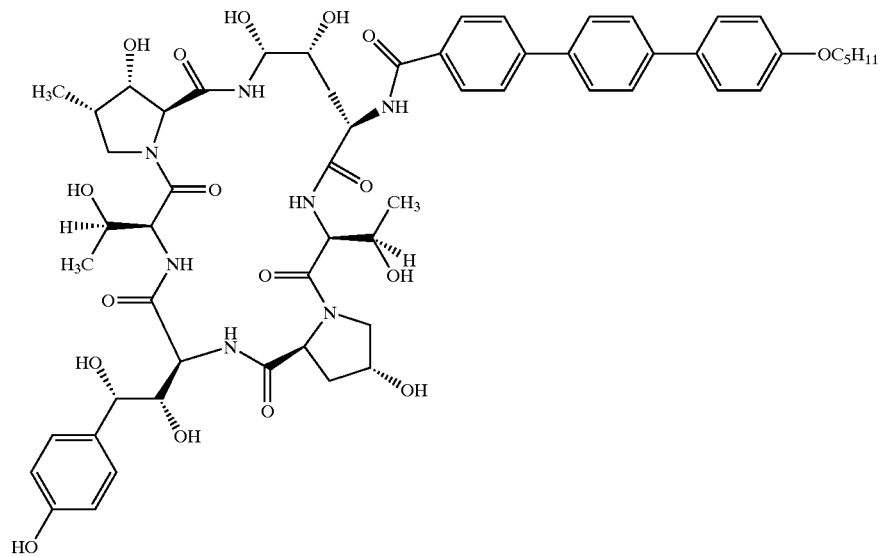

Anidulafungin the formulation. Suitable stabilizing agents include carbohydrates, such as sucrose, trehalose, fructose, and lactose, and amino acids. Other examples include polyoxyethylenesorbitan fatty esters (polysorbates), e.g., polysorbate 80 (polyoxyethylene sorbitan monooleate, Tween 80), polysorbate 40 and polysorbate 20.

Solid formulations may optionally contain a solubilizing agent or surfactant. The solid formulations may contain a solubilizing agent at a concentration of 10 to 50% w/w, 20 to 30% w/w, or e.g., 24% w/w. Suitable solubilizing agents include cetrimide, docusate sodium, glyceryl monooleate, sodium lauryl sulfate, and sorbitan esters. Exemplary solubilizing agents include polysorbates (e.g. polysorbate 20, polysorbate 40, polysorbate 80).

As used herein, "w/w" refers to percent weight in weight, and expresses the number of g of a constituent in 100 g of solution or mixture.

As used herein, "w/v" refers to percent weight in volume and expresses the number of g of a constituent in 100 mL of solution.

Solid formulations may also optionally contain a buffer. The buffer is optionally present at a concentration in the range from about 0.3 to 5%, or about 0.9% to 1.3%, or about 1.1% w/w. The term "buffer" refers to a pharmaceutically acceptable excipient that helps to maintain the pH of the solution within a particular range specific to the buffering system. Suitable buffers include acetates, citrates, phosphates, tartrates, lactates, succinates, amino acids and the like.

When freeze dried, the formulations may optionally contain a bulking agent. The term "bulking agent" refers to a pharmaceutically acceptable excipient that adds bulk to a formulation which results in a well-formed cake upon freeze drying. Suitable bulking agents include mannitol, glycine, lactose, sucrose, trehalose, dextran, hydroxyethyl starch, ficoll and gelatin. The bulking agent is for example present in the formulation at the concentration in the range from about 30 to 68% w/w of the solid formulation. For example, the formulation comprises about 43 to 52% and optionally about 48% w/w bulking agent The solid formulations may be prepared using conventional dissolution and mixing procedures. For example, the anidulafungin is dissolved in a non-toxic aqueous solvent optionally in the presence of a pharmaceutically acceptable polyethylene glycol or propylene glycol and optionally one or more bulking agents, buffers, and/or stabilizing agents. The resulting solution is then sterilized, e.g., sterile filtered and preferably lyophilized to provide the desired formulation.

The solution to be lyophilized may further include one or more antioxidants, such as acetone sodium bisulfite, bisulfite sodium, butylated hydroxy anisole, butylated hydroxy toluene, cystein, cysteinate HCl, dithionite sodium, gentisic acid, gentisic acid ethanolamine, glutamate monosodium, formaldehyde sulfoxylate sodium, metabisulfite potassium, metabisulfite sodium, monothioglycerol, propyl gallate, sulfite sodium, thioglycolate sodium, and ascorbic acid.

The solid composition also may include a tonicity agent such as glycerin, lactose, mannitol, dextrose, sodium chloride, sodium sulfate and sorbitol.

The solution to be lyophilized may include excipients, stabilizing agents, buffers, tonicity agents, and antioxidants, as described above, and may further contain agents which modify the physical appearance and shape of the lyophilized solid such as mannitol, fructose, and tartaric acid. Solid compositions obtained from lyophilization of the solution may include amounts of all species described herein. Further solvents, solvent mixtures, or solvent systems are reviewed in, S. Nema et al, *PDA Journal of Pharm. Science and Tech.* 51(4): 166–171 (1997). The solution to be lyophilized may be sterilized prior to lyophilization. Alternatively, the solid product from lyophilization may be sterilized. Methods for sterilization are reviewed in *Remington's Pharmaceutical Sciences*, 18th ed. (1990).

A suitable method for freeze-drying is described in Nail et al. Freeze Drying Principles and Practice, in Pharmaceutical Dosage Forms, $2^{nd}$ Ed., Marcel Dekker, Inc. NY, pp. 163–233 (1993). The formulation is preferably freeze-dried in a vial which can then be stored until needed. A non-toxic, aqueous solvent is added to the vial to dissolve the freeze-dried material thus forming a solution that can be used in a parenteral therapeutic application. Those skilled in the art will appreciate that the aqueous solvent includes other common solutions used in such applications (e.g., saline solutions, dextrose solutions, etc.). In application, the formulations are typically diluted or reconstituted (if freeze-dried) and may be further diluted if necessary, prior to administration.

The active ingredient is typically formulated into pharmaceutical dosage forms to provide an easily controllable dosage of the drug and to give the patient an elegant and easily handleable product. Solid formulations may comprise for example, about 0.1% to 60% w/w of active ingredient for example, anidulafungin, or about 1% to 30% w/w, or about 8.0 to 12% w/w, or optionally about 9–10% w/w.

As used herein, the term "unit dose" or "unit dosage" refers to physically discrete units that contain a predetermined quantity of active ingredient calculated to produce a desired therapeutic effect. When a unit dose is administered parenterally, it is typically provided in the form of measured units in ampoules (or vials). The dosage to be administered may vary depending upon the physical characteristics of the patient, the severity of the patient's symptoms, and the means used to administer the drug. The specific dose for a given patient is usually set by the judgment of the attending physician. Dosages can be for example, about 5–500 mg or about 35–200 mg daily administered from an intravenous injection (IV).

Suitable carriers, diluents and excipients are known in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the active ingredient is being applied. The formulations may also include wetting agents, lubricating agents, emulsifiers, suspending agents, preservatives, sweeteners, perfuming agents, flavoring agents and combinations thereof.

Shelf life of the solid compositions is the length of time that the solid composition may be stored in a form intended for a parenteral preparation and still be reconstituted in a reasonable time. The shelf life can begin when the active drug ingredient of the solid composition is made, and can end when the solid composition cannot be reconstituted in a reasonable time by a particular method or when the drug degrades or otherwise cannot be used. Solid compositions with long shelf life, for example, greater than 12 months; or greater than about 15, 20, 25, 30, 35, 36 months or more are preferred. As disclosed herein, the solvent added to the solid composition to make the parenteral formulation can increase the shelf life, to, for example, greater than 12 months; or greater than 15, 20, 25, 30, 35, 36 months or more.

An example of solid formulations for a 35 and 50 mg dose of anidulafungin is shown in Table A. This Table shows an exemplary amount as well as an optional range shown in parentheses of components of a solid formulation. These formulations are made in one embodiment by dissolving the ingredients in sterile water (e.g., 3–15 ml), optionally adjusting the pH with and freeze drying.

TABLE A

Solid Anidulafungin Formulations

| Ingredient | Quantity in mg per vial 50 mg dose (mg range) | Quantity in mg per vial 35 mg dose (range) | Function | % w/w (range) |
|---|---|---|---|---|
| Anidulafungin | 50 (40–60) | 35 (28–42) | Active Ingredient | 9.5 (7.6–11.5) |
| Fructose | 50 (45–55) | 35 (31.5–38.5) | Stabiliser | 9.5 (8.6–10.5) |
| Mannitol | 250 (225–275) | 175 (157–192) | Bulking Agent | 48 (43–52) |
| Polysorbate 80 | 125 (113–137) | 87.5 mg (79–96) | Solubilizing Agent/ surfactant | 24 (21–26) |
| Tartaric Acid | 5.6 (5.0–6.1) | 3.94 (3.5–4.3) | Buffer | 1.1 (0.9–1.3) |
| Sodium Hydroxide | | As needed | To adjust pH | negligible |
| Hydrochloric Acid | | As needed | To adjust pH | negligible |

The solid or liquid formulations in a freeze dried dosage vial may include an excess of about 1–5%, e.g., 2.5% of any one or more of the above components to allow for withdrawal of the required amount of the anidulafungin from the vial after addition of solvent and extraction for parenteral administration.

In application, the formulations are reconstituted (if lyophilized) and are further diluted prior to administration. An example of reconstitution instructions for a freeze-dried product is to add aqueous ethanolic solvent to the vial and agitate to dissolve. Typical reconstitution times are less than ten minutes, or less than one minute The resulting solution may be then further diluted in an infusion solution such as dextrose 5% in water (D5W), prior to intravenous administration.

A pharmaceutical composition may be administered using a variety of methods. Suitable methods include injection. The particular treatment method used will depend upon the type of infection being addressed.

Liquid Pharmaceutical Formulations

Provided are parenteral pharmaceutical formulations comprising anidulafungin and an aqueous solvent, wherein the formulation includes from about 5% ethanol w/w to about 50 percent ethanol w/w. The aqueous solvent, is for example, water, or e.g. saline.

As used herein, "w/w" refers to percent weight in weight, and expresses the number of g of a constituent in 100 g of solution or mixture.

Also provided are pharmaceutically acceptable parenteral formulations comprising anidulafungin and an aqueous solvent, wherein the formulation includes about 5% to about 50% w/w ethanol, e.g., about 10 to 40%; about 15 to 30%; or about 20% w/w ethanol.

Also provided are pharmaceutically acceptable parenteral formulations comprising anidulafungin and an aqueous solvent, wherein the formulation includes about 5 to 50% (w/w) propylene glycol and/or polyethylene glycol (PEG) in an aqueous ethanol solution. These formulations may be further diluted with 5% Dextrose in Water (D5W) prior to intravenous (IV) injection.

The pharmaceutical parenteral formulations may be provided in dosage vessels which contain dosage units, for example, about 5 mg to 500 mg of anidulafungin, about 20 to 200 mg, or about 35 mg, 50 mg, or 100 mg. The dosage vessels are often loaded with a slight excess, for example 2.5% excess of drug, because it is generally not possible to remove all the drug from the vial after reconstitution of the drug. For example, a 35 mg vessel may be loaded with about 36 mg of drug. A dosage unit may be provided in a sealed container, often made of Type I glass, which maintains a sterile environment for the solid product from lyophilization. For example, a vial hermetically sealed with a sterile rubber or plastic closure or stopper. The closure or stopper allows charging the vial with solvent or diluent, such as sterile Water for Injection, USP, ethanol, Normal Saline, USP, or 5% Dextrose in Water, USP.

A pharmaceutically acceptable parenteral liquid product formulation may be prepared by reconstitution of a solid composition such as a freeze dried solid composition, for example, as described above. These product liquids may be sterilized during, or after reconstitution. The reconstitution product may be used to parenterally administer an echinocandin active compound, such as anidulafungin. Reconstitution may be accomplished by charging a vessel containing the solid composition with a physiologically acceptable sterile solvent or diluent and mixing the contents of the vessel for an acceptable reconstitution time by hand shaking or swirling. Other methods of shaking or mixing the vessel may be used, for example, any mechanical shaking or reciprocating mixing device. The intensity of shaking or mixing is sufficient to reconstitute the solid composition into a liquid product in a reasonable time, for example, within a few minutes, for example, without causing severe foaming.

The reconstitution time of the solid composition, when reconstituted with one of the aqueous formulations comprising ethanol described herein, may be much less than the reconstitution time of the solid composition when reconstituted with water. The reconstitution may be carried out with an aqueous solution and ethanol as well as one or more additives, to provide a pharmaceutically acceptable parenteral formulations.

Reconstitution time is, for example, less than 10 minutes, less than 5, minutes, less than 2 minutes, less than one minute, or less than 45 seconds, for example after storage of a freeze dried drug formulation for more than one year, more than two years or more than three years. Preferably, the liquid drug formulation after reconstitution includes no more than a pharmaceutically acceptable amount of particulate matter. For example, the content of particulate matter after dissolving 35 mg of drug in 10 ml of aqueous ethanolic solvent, after freeze drying and storage, for example, after one, two or three years, is less than 6000, preferably less than 400 10 $\mu$m particles, and/or less than 600, preferably less than 200 25 $\mu$m particles.

The addition of surfactant or solubilizing agent, for example polyoxyethylene sorbitan monooleate (Tween 80 or polysorbate 80), improves solubility but can cause foaming, which reduces exposure of the drug to the solution and can cause less drug to be dissolved. Insolubility problems increase with increasing storage time of a freeze dried material. Particles can be dispersed on top of the solution in the bubbles of the foam which makes it difficult to see in the vial if the drug is dissolved. For example, when Tween 80 is added to increase the solubility of anidulafungin, and the drug is freeze dried to enhance stability, the ability to redissolve the freeze dried formulation in water becomes increasingly reduced over time. The formulations of the present invention overcome this disadvantage. The ethanol in the reconstitution solution can act by reducing the surface tension of the reconstituted drug formulation resulting in reduced foaming. This procedure also reduces reconstitution time, due to the solubility properties of ethanol.

Another advantage is that reconstitution is greatly improved in solid formulations stored longer than one year. The surfactants become less effective over time and increased foaming is observed in reconstituted drug formulations stored 18 months or longer using water for reconstitution without ethanol. This may restore surfactant function of stored solid drug formulations.

In one embodiment, the pharmaceutically acceptable parenteral formulation of echinocandin, such as anidulafungin, may have about 5 to 50% w/v ethanol, e.g., ethanol USP, in water, or 20% w/v ethanol in water or other aqueous solution. In these pharmaceutically acceptable parenteral aqueous formulations, the % w/v ethanol, such as ethanol USP may be, for example, about 5 to about 50 percent w/v; e.g. about 10 to about 40%; about 15 to about 30%; about 18 to 22 percent; or about 20 percent w/v ethanol.

Tables B and C show examples of liquid formulations of anidulafungin, where the formulations include, water, ethanol, anidulafungin and optionally one or more of the other components listed in the Tables; as well as exemplary ranges of the components. These liquid formulations may be further diluted in D5W or other aqueous diluent for intravenous injection.

TABLE B

Liquid Formulations of Anidulafungin

| Ingredient | Quantity per vial 35 mg dose in 10 ml (range) | % w/v (range) |
|---|---|---|
| Anidulafungin | 35 mg | 0.34 (0.1–2.0) |
| Fructose | 35 mg | 0.34 (0.1–1.0) |
| Mannitol | 175 mg | 1.75 (0.1–10) |
| Polysorbate 80 (Tween 80) | 87.5 mg | 0.85 (0.1–5.0) |
| Tartaric Acid | 3.94 mg | 0.04 (0.01–5.0) |
| Sodium Hydroxide | As needed | negligible |
| Hydrochloric Acid | As needed | negligible |
| Ethanol | 2 g | 20 (5–50) |
| PEG and/or propylene glycol | 1 g | 10 (0–50) |
| Sterile Water for Injection | q.s to 10 ml | to volume |

TABLE C

Optional Ranges of Liquid Formulations of Anidulafungin

| Ingredient | % wgt./wgt. range |
|---|---|
| Anidulafungin | 0.27–0.42 |
| Fructose | 0.3–0.39 |
| Mannitol | 1.6–1.9 |
| Polysorbate 80 | 0.75–0.96 |
| Tartaric Acid | 0.033–0.043 |

TABLE C-continued

Optional Ranges of Liquid Formulations of Anidulafungin

| Ingredient | % wgt./wgt. range |
|---|---|
| Sodium Hydroxide | — |
| Hydrochloric Acid | — |
| Ethanol | 5–30 |
| PEG and/or propylene glycol | 5–30 |
| Sterile Water for Injection | to volume |

In a pharmaceutically acceptable aqueous parenteral formulation of an echinocandin, such as anidulafungin, the weight percent of polyethylene glycol or propylene glycol, if present, may be, e.g., 5 to 50%; or about 20% w/v in an aqueous solvent such as water or an water-ethanol mixture.

The molecular weight of the polyethylene glycol may be less than about 1500, often less than about 1000, sometimes less than about 600, and sometimes less than about 400. Polyethylene glycol having molecular weight in the range 400–600 may be optimal. In a pharmaceutically acceptable parenteral formulation of echinocandin, such as anidulafungin, the weight percent of polyethylene glycol may be for example about 5 to 50% w/v or about 10 to 20% w/v in an aqueous solvent comprising ethanol.

A pharmaceutically acceptable parenteral formulation of echinocandin such as anidulafungin can include about 10% w/v ethanol and 10% w/v propylene glycol or polyethylene glycol in an aqueous solution such as water. In the pharmaceutically acceptable parenteral formulations, in one embodiment the sum of the percent w/v is less than or equal to 50.

The formulation can for example include an echinocandin such as anidulafungin at a concentration of about 0.1 to 2.0% w/v or about 0.25 to 0.45% w/v or optionally 0.34% w/v.

In reconstitution of the solid composition with an aqueous ethanol mixture after a long storage period of e.g. greater than one year, two years, three years or more, the mixing or shaking time for reconstitution may be less than about 400 seconds, often less than about 300 seconds, sometimes less than about 200 seconds, sometimes less than about 100 seconds, and sometimes less than about 75 seconds, wherein results may be improved in comparison to results using aqueous solvents without ethanol.

Formulations may optionally contain a stabilizing agent. A stabilizing agent is present optionally at a concentration for example, in the range of about 0.3% to about 40% w/v, or about 1% to about 10% w/v. The term "stabilizing agent" refers to a pharmaceutically acceptable excipient that enhances the chemical or physical stability of the active ingredient in the formulation. Suitable stabilizing agents include carbohydrates (e.g., as sucrose, trehalose, fructose, lactose and mannitol), and amino acids.

Formulations may also optionally contain a solubilizing agent. The solubilizing agent is present, for example, at a concentration of about 0.2% to about 2.0% w/v, or about 0.75% to about 1.0% w/v. Suitable solubilizing agents include polysorbates (eg polysorbate 20, polysorbate 40, and polysorbate 80).

Formulations may also optionally contain a buffer. The buffer is present for example at a concentration in the range from about 0.03% to about 5.0% w/v, or about 0.1% to about 2.0% w/v. The term "buffer" refers to a pharmaceutically acceptable excipient that maintains the pH of the solution within a particular range specific to the buffering system.

Formulations may have, for example, a pH of about 3.0–7.0, optionally about 4.0–6.0, or about 4.4–4.6. Suitable buffers include acetates, citrates, phosphates, tartrates, lactates, succinates, amino acids and the like. Sodium hydroxide and/or hydrochloric acid can be used to adjust the pH.

Formulations may optionally contain a bulking agent. The bulking agent is for example present in a formulation at a concentration in the range from about 1% to about 60% w/v, or about 3% to about 50% w/v. The term "bulking agent" refers to a pharmaceutically acceptable excipient that adds bulk to a formulation which results in a well-formed cake upon freeze drying. Suitable bulking agents include mannitol, glycine, lactose, sucrose, trehalose, dextran, hydroxyethyl starch, ficoll and gelatin. Preferred bulking agents include mannitol, sucrose, trehalose, lactose and combinations thereof.

Formulations may further include one or more antioxidants. The antioxidant is for example present in a formulation at a concentration range of 0.01–10% w/v or about 1–5% w/v. Examples of antioxidants include acetone sodium bisulfite, bisulfite sodium, butylated hydroxy anisole, butylated hydroxy toluene, cystein, cysteinate HCl, dithionite sodium, gentisic acid, gentisic acid ethanolamine, glutamate monosodium, formaldehyde sulfoxylate sodium, metabisulfite potassium, metabisulfite sodium, monothioglycerol, propyl gallate, sulfite sodium, thioglycolate sodium, and ascorbic acid.

In application, the formulation is typically reconstituted and further diluted if necessary, prior to administration. An example of reconstitution instructions for the lyophilized product are to add solvent to the vial and agitated to dissolve. Typical reconstitution times are less than 400 seconds. Suitable solvents include ethanol in water. In one example, the solvent is about 20 weight percent ethanol in an aqueous solution such as water. The resulting solution is optionally further diluted in an infusion solution such as dextrose 5% in water (D5W), prior to administration.

A solid composition may be reconstituted to provide a liquid product for parenteral administration to a patient. Solid compositions to be reconstituted may be provided in dosage vessels which contain dosage units, for example, from about 5 mg to about 500 mg of echinocandin, such as anidulafungin, for example about 15 mg, about 25 mg, about 35 mg, about 50 mg, about 100 mg, or about 200 mg. The dosage vessels are often loaded with a slight excess, for example 2.5% excess of drug, because it is generally not possible to extract all the drug upon use of the reconstituted drug. For example, a 35 mg vessel may be loaded with about 36 mg of drug. A dosage unit may be provided in a sealed container, often made of Type I glass, which maintains a sterile environment for the solid product from lyophilization, for example, a 50 ml vial hermetically sealed with a sterile rubber or plastic closure or stopper.

The solid product, for example, 35 mg of anidulafungin, and optionally other components of the formulation, in a 10 mL vial, or 50 mg anidulafungin in a 15 mL vial, can be reconstituted in a pharmaceutically acceptable diluent, for example 5–50% w/v ethanol or 20% w/v ethanol in Sterile Water for Injection (SWFI) to a concentration of drug that is for example about 0.5–5 mg/mL, about 3–4 mg/ml or about 3.3 mg/ml. The reconstituted drug is then further diluted about 5–10 fold or about 7 fold with a pharmaceutically acceptable diluent such as 5% Dextrose in water (D5W), to a concentration of, e.g., 0.1 to 3 mg/mL or about 0.5 mg/mL for administration. This solution can be administered intravenously.

The following examples are provided to illustrate but not limit the invention.

All documents, including publications, treatises, articles, patents and patent applications referenced herein are incorporated herein by reference in their entirety.

EXAMPLES

Example 1

Method of Manufacture of Solid Anidulafungin Formulation

Manufacture

In a suitable manufacturing vessel, 25 grams of polysorbate 80, are added to a sufficient amount of deoxygenated Sterile Water for Injection and mixed slowly until dissolved. The solution is cooled and 1.1 gram of tartaric acid is added. The solution is adjusted to pH 4.5 using a sodium hydroxide solution and/or a hydrochloric acid solution.

10 grams of anidulafungin are added to a suitable vessel with Sterile Water for Injection and swirled to generate a slurry. The resulting slurry is added to the bulk polysorbate 80 buffer solution and the liquid is mixed until all the slurried drug is dissolved. The fructose (10 grams) and mannitol (50 grams) are added and mixed until dissolved. Additional Sterile Water for Injection is added to bring the solution to final volume. The pH of the final solution is determined and adjusted, if necessary, to pH 4.5. The solution is sterilized by membrane filtration using two redundant in-line 0.22$\mu$ Millipak 20 filters into a Class 100 aseptic area. These membrane filters are non-asbestos, non-fiber releasing, and meet cGMP requirements for use in the manufacture and processing of components of drug products for parenteral injection in humans. Sterilizing filters are integrity tested after use to assure that integrity was maintained during filtration. In-process testing occurs on the bulk material after the filtration for Appearance, Anidulafungin concentration, and pH.

Lyophilization

Aliquots (3.5 ml) of the sterile filtered bulk solution are aseptically filled into the sterile (depyrogenated) glass vials and sterile stoppers are partially inserted. The filled vials are transferred to the freeze dryer and lyophilized.

The freeze drying process is monitored by thermocouple probes of representative vials. Vials are loaded into the freeze dryer and the temperature is gradually reduced until all thermocouples reach −40° C. After the desired time has elapsed, the air in the chamber is evacuated and the temperature gradually increased until the shelf temperature is approximately +35° C. The samples are held at about +35° C. for 6–8 hours. The chamber is then restored to atmospheric pressure with filtered Nitrogen UHP and the stoppers are seated. Vials are removed and capped with aluminum seals.

During aseptic operations such as set-up, filtration, filling and stoppering, the air is monitored for microbial content with settling plates and volumetric air sampler. In addition, operators and surfaces are monitored by contact plates. The air is monitored for particles using a particle counter. Records of the results of these surveys are evaluated against pre-established action limits for the area involved and, if necessary, an investigation is conducted. Appropriate action is taken when indicated by the results of the investigation.

All components and equipment are sterilized by appropriate processes. Sterilization processes uses the "overkill"

approach for both steam and dry heat sterilization cycles. The cycle for steam autoclaving is for 30 minutes at 121° C. and the cycle for dry heat sterilization is for at least three hours at >250° C. The resulting solid is stored at room temperature.

Reconstitution

Reconstitution occurs in a two step process. In the first step, the solid formulation containing 35 mg anidulafungin, and optionally other components of the formulation, is reconstituted in a 10 ml solution of 20% w/v ethanol in Sterile Water for Injection. The mixture is swirled by hand for 100 seconds and observed to confirm the complete dissolution of the solid product in a clear bubble free solution. This mixture is then diluted 7 fold in a solution of 5% Dextrose in Sterile Water (D5W). The resulting solution is now available for IV injection.

Example 2

Reconstitution Time of Solid Anidulafungin Compositions

A: Reconstitution Time of Anidulafungin Stored for up to 36 Months

Solid compositions containing 1) 35 mg anidulafungin (lot CT12759, PPD04365), 175 mg mannitol USP, 87.5 mg polysorbate 80 NF, 35 mg fructose USP, and 3.95 mg tartaric acid NF as a buffer; or 2) 25 mg (lot CT12758) anidulafungin, 125 mg mannitol USP, 62.5 mg polysorbate 80 NF, 25 mg fructose USP, and 2.5 mg tartaric acid NF as a buffer, were tested to determine reconstitution time after storage. The samples of lyophilized formulations, obtained from Eli Lilly (Indianapolis, Ind.), were stored in solid form for up to 36 months or longer. Storage conditions were 25° C., or 5° C. 60% relative humidity (RH). The reconstitution time assay consisted of initiating reconstitution of the solid composition by injecting 10 ml of solvent into the vial containing 35 mg of anidulafungin and 7 ml of solvent into the vial containing 25 mg of anidulafungin. Once the solvent was added, it was immediately mixed in the vial by gently shaking or swirling by hand. Every 10 seconds shaking was stopped and the vial was visually inspected until completeness of solution was observed. The results in Table 1 show each reconstitution time reported represented as an average of 5 replicates. It can be seen from the Tables that the addition of ethanol to the reconstitution mixture significantly reduces the reconstitution time of anidulafungin.

A comparison was made between shaken and swirled (by hand) reconstitution methods. Swirling generally results in longer reconstitution times, but is used to reduce foaming. By shaking the diluent, reconstitution times are shortened, but foaming can often occur with the use of water alone. Using aqueous ethanol as a diluent, it is possible to use shaking to dissolve the drug quickly, and foaming is reduced.

As illustrated in Table 1, reconstitution of solid compositions containing anidulafungin was significantly reduced from greater than 5400 seconds to 74 seconds using 20% w/w ethanol in water in comparison with pure water.

TABLE 1

Reconstitution Times of Solid Compositions Containing Anidulafungin Shaken in Indicated Diluent

| Storage Condition | Lot No. | Storage Time | Time‡ (Seconds) | diluent* |
|---|---|---|---|---|
| Initial | CT12758 | Initial | 24 | Water |
| 25° C./60% RH | CT12758 | 3 month | 164 | Water |
| 25° C./60% RH | CT12758 | 18 month | 338 | Water |
| 25° C./60% RH | CT12758 | 25 month | >5400 | Water |
| 25° C./60% RH | CT12758 | 36 month | >5400** | Water |
| Initial | PPD04365 | Initial | 27 | Water |
| 25° C./60% RH | PPD04365 | 3 month | 101 | Water |
| 25° C./60% RH | PPD04365 | 18 month | 271 | Water |
| 25° C./60% RH | PPD04365 | 25 month | >5400 | Water |
| Initial | CT12759 | Initial | 32 | Water |
| 25° C./60% RH | CT12759 | 3 month | 64 | Water |
| 25° C./60% RH | CT12759 | 18 month | 247 | Water |
| 25° C./60% RH | CT12759 | 25 month | >5400** | Water |
| 25° C./60% RH | CT12759 | 36 month | >5400** | Water |
| 25° C./60% RH | CT12759 | 32 months | 74 | Aqueous Ethanol |

‡values represent the average of 5 repeats
*water is sterile water filtered for injection (SWFI); aqueous ethanol is 20% w/w ethanol in SWFI.
**Method modification: mechanical platform shaker used, room temperature
RH = relative humidity Tables 2 and 3 show a comparison of reconstitution times for different lots of solid anidulafungin compositions in water and aqueous ethanol, where, advantageously, drug could be dissolved in 120 seconds or less with shaking using aqueous ethanol. Generally using water, shaking produces unwanted foaming. Swirling can be used to reduce foaming, but the length of reconstitution time can increase considerably. Reconstitution time using water and shaking varied between 150 and 360 seconds. Reconstitution times using water and swirling, varied between 240 and 1200 seconds. The reconstitution time using water and ethanol and shaking is between 60 and 120 seconds and is significantly reduced relative to reconstitution in water. Thus, using a water/ethanol mixture results less foaming and a reduced reconstitution time.

TABLE 2

Reconstitution Times for Lot 12758 Stored for 3 Years at 5° C.

| Lot No. | Vial | Diluent* | Agitation | Time (seconds) | Final Reconstitution Evaluation |
|---|---|---|---|---|---|
| Swirled | | | | | |
| CT12758 | 1 | Water | Swirled | 1200 | Hazy, with a significant number of small particles |
| CT12758 | 2 | Water | Swirled | 600 | Completely in solution |
| CT12758 | 3 | Water | Swirled | 1200 | Clear solution with a small number of large particles |

TABLE 2-continued

Reconstitution Times for Lot 12758 Stored for 3 Years at 5° C.

| Lot No. | Vial | Diluent* | Agitation | Time (seconds) | Final Reconstitution Evaluation |
|---|---|---|---|---|---|
| CT12758 | 4 | Water | Swirled | 1200 | Clear solution with a small number of small particles |
| CT12758 Shaken | 5 | Water | Swirled | 720 | Completely in solution |
| CT12758 | 1 | Water | Shaken | 360 | Completely in solution |
| CT12758 | 2 | Water | Shaken | 330 | Completely in solution |
| CT12758 | 3 | Water | Shaken | 330 | Completely in solution |
| CT12758 | 4 | Water | Shaken | 360 | Completely in solution |
| CT12758 Swirled | 5 | Water | Shaken | 330 | Completely in solution |
| CT12758 | 1 | Aqueous Ethanol | Swirled | 300 | Completely in solution |
| CT12758 | 2 | Aqueous Ethanol | Swirled | 300 | Completely in solution |
| CT12758 | 3 | Aqueous Ethanol | Swirled | 300 | Completely in solution |
| CT12758 | 4 | Aqueous Ethanol | Swirled | 300 | Completely in solution |
| CT12758 Shaken | 5 | Aqueous Ethanol | Swirled | 300 | Completely in solution |
| CT12758 | 1 | Aqueous Ethanol | Shaken | 120 | Completely in solution |
| CT12758 | 2 | Aqueous Ethanol | Shaken | 120 | Completely in solution |
| CT12758 | 3 | Aqueous Ethanol | Shaken | 120 | Completely in solution |
| CT12758 | 4 | Aqueous Ethanol | Shaken | 60 | Completely in solution |
| CT12758 | 5 | Aqueous Ethanol | Shaken | 120 | Completely in solution |

*water is-sterile water filtered for injection (SWFI), aqueous ethanol is 20% ethanol w/w in SWFI

TABLE 3

Reconstitution Times for Lot 12759 Stored for 3 Years at 5° C.

| Lot | Vial | Diluent* | Agitation | Time(s) | Final Reconstitution Evaluation |
|---|---|---|---|---|---|
| Swirled | | | | | |
| CT12759 | 1 | Water | Swirled | 480 | Completely in solution |
| CT12759 | 2 | Water | Swirled | 600 | Completely in solution |
| CT12759 | 3 | Water | Swirled | 480 | Completely in solution |
| CT12759 | 4 | Water | Swirled | 720 | Completely in solution |
| CT12758 Shaken | 5 | Water | Swirled | 240 | Completely in solution |
| CT12759 | 1 | Water | Shaken | 150 | Completely in solution |
| CT12759 | 2 | Water | Shaken | 150 | Completely in solution |
| CT12759 | 3 | Water | Shaken | 150 | Completely in solution |
| CT12759 | 4 | Water | Shaken | 180 | Completely in solution |
| CT12758 Swirled | 5 | Water | Shaken | 180 | Completely in solution |
| CT12759 | 1 | Aqueous Ethanol | Swirled | 240 | Completely in solution |
| CT12759 | 2 | Aqueous Ethanol | Swirled | 300 | Completely in solution |
| CT12759 | 3 | Aqueous Ethanol | Swirled | 300 | Completely in solution |
| CT12759 | 4 | Aqueous Ethanol | Swirled | 300 | Completely in solution |
| CT12758 Shaken | 5 | Aqueous Ethanol | Swirled | 300 | Completely in solution |
| CT12759 | 1 | Aqueous Ethanol | Shaken | 60 | Completely in solution |
| CT12759 | 2 | Aqueous Ethanol | Shaken | 60 | Completely in solution |
| CT12759 | 3 | Aqueous Ethanol | Shaken | 60 | Completely in solution |
| CT12759 | 4 | Aqueous Ethanol | Shaken | 90 | Completely in solution |
| CT12758 | 5 | Aqueous Ethanol | Shaken | 60 | Completely in solution |

*water is-sterile water filtered for injection, aqueous ethanol is 20% ethanol w/w in SWFI B: Reconstitution Times for Anidulafungin Stored for 42 Months Solid compositions containing 1) 35 mg (lot CT12759) anidulafungin, 175 mg mannitol USP, 87.5 mg polysorbate 80 NF, 35 mg fructose USP, and 3.95 mg tartaric acid NF as a buffer; or 2) 25 mg (lot CT12758) anidulafungin, 125 mg mannitol USP, 62.5 mg polysorbate 80 NF, 25 mg fructose USP, and 2.5 mg tartaric acid NF as a buffer, were tested to determine reconstitution time after storage. These samples of lyophilized formulations, obtained from Eli Lilly (Indianapolis, Ind.), were stored in solid form for 42 months. Storage conditions were 25° C., 60% relative humidity (RH). The reconstitution time assay consisted of initiating reconstitution of the solid composition by injecting 10 ml of solvent into the vial containing 35 mg of anidulafungin and 7 ml of solvent into the vial containing 25 mg of anidulafungin. Once the solvent was added, it was immediately mixed in the vial by gently shaking or swirling by hand. Every 10 seconds shaking was stopped and the vial was visually inspected. The assay was stopped after 1200 seconds and the samples were visually evaluated for clarity and completeness of solution. Samples that appeared completely dissolved were further evaluated for particulate matter by a light obscuration assay described in USP 23 Section 788.

The results in Tables 4 and 5 show each reconstitution time for 3 different vials for each lot in water that was shaken or swirled and in a 20% (w/w) ethanol in water solution that was shaken. The Tables also show a description of the final reconstitution evaluation. It can be seen that the addition of ethanol to the reconstitution mixture enables the complete reconstitution of anidulafungin samples stored for 42 months after only 200 or 300 seconds of swirling. Samples from identical lots were not completely dissolved in pure water after 1200 seconds of shaking or swirling. The solutions resulting from reconstitution in aqueous ethanol were also significantly clearer and showed no foaming or particulate matter in contrast to the corresponding water solutions. Measurements of particulate matter of samples reconstituted in aqueous ethanol from lot CT12758 show only 95 particles greater than 10 µm in size and only 12 particles greater than 25 µm in size. Samples from lot CT12759 reconstituted in aqueous ethanol showed similarly small numbers of particles, 67 and 4 particles greater than 10 and 25 µm in size respectively. This significantly smaller than the USP specification of 6000 and 600 particles 10 and 25 µm in size.

The samples dissolved in water were hazy and showed significant particulate matter visible to the naked eye and therefore contained well over the level of particulate matter to be accurately measured by the light obscuration method. The samples reconstituted in aqueous ethanol diluent were shaken, not swirled. This method results in significant foaming when used with pure water as the diluent. The results were consistent for both of the drug lots that were evaluated. The aqueous ethanol mixture acts to both reduce reconstitution time and reduce foaming of the reconstituted anidulafungin samples stored for as long as 42 months.

TABLE 4

Reconstitution times for Lot CT12758 (25 mg/vial) stored for 42 months at 25° C./60% RH

| Lot# | Vial | Diluent | Agitation | Time (seconds) | Final Reconstitution Evaluation |
|---|---|---|---|---|---|
| CT12758 | 1 | Water* | Swirled | 1200 | Hazy, large particles observed |
| CT12758 | 2 | Water* | Swirled | 1200 | Hazy, large particles observed |
| CT12758 | 3 | Water* | Swirled | 1200 | Hazy, large particles observed |
| CT12758 | 1 | Water* | Shaken | 1200 | Hazy and foamy, with a significant number of small particles |
| CT 12758 | 2 | Water* | Shaken | 1200 | Hazy and foamy, with a significant number of small particles |
| CT12758 | 3 | Water* | Shaken | 1200 | Hazy and foamy, with a significant number of small particles |
| CT12758 | 1 | Aq. EtOH** | Shaken | 200 | Completely in solution |
| CT12758 | 2 | Aq. EtOH** | Shaken | 200 | Comletely in solution |
| CT12758 | 3 | Aq. EtOH** | Shaken | 200 | Completely in solution |

*Water is sterile water filtered for injection (SWFI)
**Aq. EtOH = 20% (w/w) Ethanol/Water

TABLE 5

Reconstitution times for Lot CT12759 (35 mg/vial) stored for 42 months at 25° C./60% RH

| Lots# | Vial | Diluent | Agitation | Time (seconds) | Final Reconstitution Evaluation |
|---|---|---|---|---|---|
| CT12759 | 1 | Water* | Swirled | 1200 | Clear, with a significant number of different particles |
| CT12759 | 2 | Water* | Swirled | 1200 | Clear, with a significant number of different particles |
| CT12759 | 3 | Water* | Swirled | 1200 | Clear, with a significant number of different particles |
| CT12759 | 1 | Water* | Shaken | 1200 | Hazy and foamy, with large and small particles |
| CT12759 | 2 | Water* | Shaken | 1200 | Hazy and foamy, with large and small particles |
| CT12759 | 3 | Water* | Shaken | 1200 | Hazy and foamy, with large and small particles |
| CT12759 | 1 | Aq. EtOH** | Shaken | 300 | Completely in solution |
| CT12759 | 2 | Aq. EtOH** | Shaken | 300 | Completely in solution |
| CT12759 | 3 | Aq. EtOH** | Shaken | 300 | Completely in solution |

*Water is sterile water filtered for injection (SWFI)
**Aq. EtOH = 20% (w/w) Ethanol/Water Example 3

Particulate Matter, pH, and Clarity of Reconstituted Anidulafungin

Anidulafungin solid compositions were reconstituted with 20% ethanol in water (SWFI) (w/w) or 100% water (SWFI). Solid compositions contained 1) 35 mg anidulafungin (lot CT12759), 175 mg mannitol USP, 87.5 mg polysorbate 80 NF, 35 mg fructose USP, and 3.95 mg tartaric acid NF as a buffer; or 2) 25 mg (lot CT12758) anidulafungin, 125 mg mannitol USP, 62.5 mg polysorbate 80 NF, 25 mg fructose USP, and 2.5 mg tartaric acid NF as a buffer, and had been stored in solid form for up to 36 months. The samples (from the designated Lot Nos.) were obtained from Eli Lilly (Indianapolis, Ind.) and were evaluated based on appearance of the reconstituted sample, pH, and particulate matter. Appearance was visually evaluated on the basis of color and clarity of the solution described in USP 24. The pH value was determined following the approach described in USP 24 general chapter 791. Particulate matter was measured by light obscuration as described in USP 23 Section 788. This in an instrument based assay that measures particulate matter which is typically not detectable by visual inspection. The data show that the visual appearance and pH of aqueous ethanol reconstituted samples, are virtually identical to the aqueous samples, yet particulate matter is significantly reduced. The results are shown in Table 6. Samples were evaluated at the initial time point, and after various storage periods. The samples dissolved in the ethanol-water mixture were also evaluated at 1, 4, 8, 24, and 48 hours following reconstitution. The samples were reconstituted with 10 ml (35 mg of anidulafungin) or 7 ml (25 mg anidulafungin) of ethanol:purified water (SWFI) (20:80) or 100% water (SWFI).

The results demonstrated that particulate matter was reduced with the aqueous ethanol formulation. Table 6 shows that reconstitution with aqueous ethanol after 32 months of storage resulted in only 255 10 $\mu$m particles and 16 25 $\mu$m particles identified; in contrast, an average of 747 10 $\mu$m and 107 25 $\mu$m particles were identified in the solutions that were reconstituted with pure water after only 25 months of storage. Higher numbers of particulates is undesirable for pharmaceutical administration, and greater than 6000 10 $\mu$m particles is not acceptable for pharmaceutical IV use.

TABLE 6

Appearance, pH, and Particulate Matter of Reconstituted Anidulafungin

| Storage Time (Time after reconstitution) | Appearance of Reconstituted Solution | pH | Particulate Matter (number of particles) 10 $\mu$m/ 25 $\mu$m | Lot # | Diluent |
| --- | --- | --- | --- | --- | --- |
| 32 months (Initial) | Clear solution, | 4.6 | 393/121 | CT12759 | 20:80 EtOH:H$_2$O |
| 32 months (1 hour) | Clear solution, | 4.6 | 261/6 | CT12759 | 20:80 EtOH:H$_2$O |
| 32 months (4 hours) | Clear solution, | 4.6 | 176/3 | CT12759 | 20:80 EtOH:H$_2$O |
| 32 months (8 hours) | Clear solution, | 4.7 | 238/12 | CT12759 | 20:80 EtOH:H$_2$O |
| 32 months (24 hours) | Clear solution, | 4.7 | 201/14 | CT12759 | 20:80 EtOH:H$_2$O |
| 32 months (48 hours) | Clear solution, | 4.7 | 255/16 | CT12759 | 20:80 EtOH:H$_2$O |
| 25 month (initial) | Clear solution, | 4.23 | 365/38 | CT12759 | 100% H$_2$O |
| 36 month (initial) | sample did not dissolve completely | 4.22 | 4874/264 | CT12759 | 100% H$_2$O |
| 25 month (initial) | Clear solution, | 4.36 | 888/127 | CT12758 | 100% H$_2$O |
| 36 month (initial) | Clear solution, | 4.28 | 6635/394 | CT12758 | 100% H$_2$O |
| 25 month (initial) | Clear solution, | 4.18 | 988/157 | PPD04365 | 100% H$_2$O |

Example 4

Potency and Total Related Substance TRS of Reconstituted Anidulafungin.

Solid compositions containing 1) 35 mg anidulafungin (lot CT12759), 175 mg mannitol USP, 87.5 mg polysorbate 80 NF, 35 mg fructose USP, and 3.95 mg tartaric acid NF as a buffer; or 2) 25 mg (lot CT12758) anidulafungin, 125 mg mannitol USP, 62.5 mg polysorbate 80 NF, 25 mg fructose USP, and 2.5 mg tartaric acid NF as a buffer and had been stored in solid form for up to 36 months were measured for potency and related substances. Samples (from identified Lot Nos.) were obtained from Eli Lilly. Potency (Pot) and TRS were determined using a high-pressure, liquid chromatograph (HPLC) equipped with a 15 cm×4.6 mm, 3.5 micron particle size, Zorbax™ XDB-Cl8 column. The anidulafungin samples were eluted with a 0.85% w/w aqueous phosphoric acid solution and a 95% aqueous acetonitrile solution using methanol as the diluent. A gradient elution scheme was used where the ratio of the phosphoric acid solution to the acetonitrile solution was varied from 95:5 to 59:41 to 5:95 to 95:5 over a one hour period. As can be seen in Table 7, potency and total related matter of the reconstituted anidulafungin are essentially unchanged by the addition of ethanol to the reconstitution composition relative to reconstitution in 100% water. Furthermore, data was measured for a total of 15 peaks in the HPLC chromatogram and all were essentially unchanged in the presence of ethanol.

Table 7 below illustrates the potency and related substances data. It can be seen that both the water and ethanol water mixtures exhibit the same stability over time, illustrating that ethanol did not appear to interact with or decompose the drug formulation.

TABLE 7

Potency and Total Related Substance of Reconstituted Solid Anidulafungin Formulation

| Storage Time -(Time after reconstitution) | Potency mg/vial | relative % | Total related substance % Area under curve | Lot No. | Solvent |
| --- | --- | --- | --- | --- | --- |
| 32 months (Initial) | 36.1 | 103.1 | 3.5 | CT12759 | 20:80 EtOH:H$_2$O |
| 32 months (1 hour) | 36.2 | 103.4 | 3.5 | CT12759 | 20:80 EtOH:H$_2$O |
| 32 months (4 hours) | 36.3 | 103.7 | 3.6 | CT12759 | 20:80 EtOH:H$_2$O |
| 32 months (8 hours) | 36.2 | 103.4 | 3.5 | CT12759 | 20:80 EtOH:H$_2$O |
| 32 months (24 hours) | 36.2 | 103.4 | 3.7 | CT12759 | 20:80 EtOH:H$_2$O |
| 32 months (48 hours) | 36.2 | 103.4 | 3.7 | CT12759 | 20:80 EtOH:H$_2$O |
| 25 month (initial) | 35.9 | 102.6 | 4.0 | CT12759 | 100% H$_2$O |
| 36 month (initial) | 36.2 | 103.4 | 3.5 | CT12759 | 100% H$_2$O |
| 25 month (initial) | 25.6 | 102.4 | 3.9 | CT12758 | 100% H$_2$O |
| 36 month (initial) | 26.3 | 105.2 | 3.4 | CT12758 | 100% H$_2$O |
| 25 month (initial) | 35.0 | 100.0 | 3.9 | PPD04365 | 100% H$_2$O |

Example 5

Reconstituted Anidulafungin Parenteral Products

A pharmaceutically acceptable lyophilized formulation of anidulafungin for injection is provided. For example, 35 mg or 50 mg is provided per vial. Each vial of the 35 mg dosage form contains: anidulafungin, 35 mg; mannitol USP, 175 mg; polysorbate 80 NF, 87.5 mg; fructose USP, 35 mg;

tartaric acid NF, 3.94 mg, as a buffer. Each vial of the 50 mg dosage form contains: anidulafungin, 50 mg; mannitol USP, 250 mg; polysorbate 80 NF, 125 mg; fructose USP, 50 mg; tartaric acid NF, 5.63 mg, as a buffer.

An overfill of 2.5% of the formulation is provided to permit withdrawal of the labeled amount after reconstitution. The lyophilized drug product is stored at controlled room temperature (15–30° C.). Unopened lyophilized vials of anidulafungin are preferably stored at controlled room temperature, 15–30° C. Vials are not be frozen and opened vials are not reused. Reconstituted vials or infusion bags containing anidulafungin are stored in the refrigerator, 2–8° C. Since the vials may not contain any preservative, the contents are used immediately after reconstitution. The infusion product is protected from exposure to direct sunlight.

Following reconstitution with 20% alcohol USP/80% Sterile Water for Injection USP (w/w) (10 mL for the 35 mg anidulafungin vial, and 15 mL for the 50 mg vial) anidulafungin is diluted with Dextrose Injection 5% (5% Dextrose in Water, USP) prior to use, seven fold dilution. The drug, when diluted with Dextrose Injection 5%, is stored in a refrigerator at 2 to 8° C. and used or discarded within 24 hours.

What is claimed is:

1. A kit for use in delivery of a pharmaceutically acceptable liquid parenteral pharmaceutical formulation, the kit comprising:
   a first vial containing a pharmaceutically acceptable solid formulation comprising 20 to 200 mg anidulafungin, wherein the solid formulation does not dissolve completely in water; and
   a second vial comprising a pharmaceutically acceptable aqueous solution of about 10 to 60 mL of an aqueous solution of about 10 to 30% w/v ethanol.

2. A kit for use in delivery of a pharmaceutically acceptable liquid parenteral pharmaceutical formulation, the kit comprising:
   a first vial containing a pharmaceutically acceptable solid formulation comprising 20 to 200 mg anidulafungin, wherein the solid formulation does not dissolve completely in water; and
   a second vial comprising a pharmaceutically acceptable aqueous solution, wherein the aqueous solution comprises about 10% to about 40% w/v ethanol.

3. The kit of claim 2, wherein the solution in the second vial comprises polyethylene glycol or polypropylene glycol.

4. The kit of claim 3, wherein the solution in the second vial comprises 2–20% w/v polyethylene glycol or propylene glycol.

5. The kit of claim 2, wherein the first vial further comprises polyethylene glycol or polypropylene glycol.

6. The kit of claim 5, wherein the first vial further comprises 2–20% w/v polyethylene glycol or propylene glycol.

7. A kit for use in delivery of a pharmaceutically acceptable parenteral pharmaceutical formulation, the kit comprising:
   a first vial containing a pharmaceutically acceptable solid formulation comprising anidulafungin, wherein the solid formulation does not dissolve completely in water; and
   a second vial comprising a pharmaceutically acceptable aqueous solution comprising an aqueous solvent comprising from about 10 to about 30% w/v ethanol.

8. The kit of claim 7, wherein the first vial contains a solid formulation comprising 25 to 200 mg of anidulafungin and the second vial contains 10 to 60 milliliters of aqueous solution comprising about 10 to 30% w/v ethanol.

9. The kit of claim 7, wherein the solid formulation is characterized by dissolving more rapidly in an aqueous solvent comprising from about 10% w/v to about 30% w/v ethanol than in water.

10. The kit of claim 7, wherein the first vial further comprises an additive selected from the group consisting of polyethylene glycol, propylene glycol, a stabilizing agent, a buffer, a tonicity agent and an antioxidant.

11. The kit of claim 7, wherein the second vial further comprises an additive selected from the group consisting of polyethylene glycol, propylene glycol, a stabilizing agent, a buffer, a tonicity agent and an antioxidant.

12. The kit of claim 7, wherein the first vial contains a solid formulation comprising 20 to 200 mg of anidulafungin and the second vial contains 10 to 60 milliliters of aqueous solution comprising about 10 to 30% w/v ethanol.

13. The kit of claim 12, wherein the first vial contains a solid formulation comprising a dosage unit of anidulafungin of about 50 mg or about 100 mg.

14. The kit of claim 7, wherein the solid formulation dissolves in the solution in less than about 400 seconds.

15. The kit of claim 7, wherein the solid formulation dissolves in the solution in less than about 200 seconds.

16. The kit of claim 7, wherein the solid formulation is further characterized in that upon reconstitution of a sample of about 35 mg of the solid formulation in 10 ml of aqueous solvent comprising from about 10% w/v to about 30% w/v ethanol, a reconstituted formulation so formed is visibly clear and has less than 400 10 µm particles.

17. The kit of claim 7, wherein the aqueous solvent in the second vial is water or saline.

18. The kit of claim 7, wherein the aqueous solution includes about 20% w/v ethanol.

19. The kit of claim 7, wherein the first vial further comprises about 10% to about 50% w/v of at least one of propylene glycol and polyethylene glycol.

20. The kit of claim 7, wherein the second vial further comprises about 10% to about 50% w/v of at least one of propylene glycol and polyethylene glycol.

21. The kit of claim 7, wherein the first vial further comprises a stabilizing agent.

22. The kit of claim 21, wherein the stabilizing agent is selected from the group consisting of mannitol, histidine, lysine, glycine, sucrose, fructose, trehalose, lactose and mixtures thereof.

23. The kit of claim 7, wherein the second vial further comprises a stabilizing agent.

24. The kit of claim 23, wherein the stabilizing agent is selected from the group consisting of mannitol, histidine, lysine, glycine, sucrose, fructose, trehalose, lactose and mixtures thereof.

25. The kit of claim 7, wherein the first vial further comprises a bulking agent.

26. The kit of claim 25, wherein the bulking agent is selected from the group consisting of mannitol, glycine, lactose, sucrose, trehalose, dextran, hydroxyethyl starch, ficoll and gelatin.

27. The kit of claim 7, wherein the first vial further comprises a solubilizing agent.

28. The kit of claim 27, wherein the solubilizing agent is a polysorbate.

29. The kit of claim 28, wherein the solubilizing agent is polysorbate 80.

30. The kit of claim 7, wherein the second vial further comprises a solubilizing agent.

31. The kit of claim 30, wherein the solubilizing agent is a polysorbate.

32. The kit of claim 31, wherein the solubilizing agent is polysorbate 80.

33. The kit of claim 7, wherein the first vial further comprises a buffer.

34. The kit of claim 33, wherein the buffer is selected from the group consisting of acetates, citrates, tartrates, lactates, succinates, and phosphates.

35. The kit of claim 7, wherein the second vial further comprises a buffer.

36. The kit of claim 35, wherein the buffer is selected from the group consisting of acetates, citrates, tartrates, lactates, succinates, and phosphates.

37. The kit of claim 7, wherein the first vial further comprises a tonicity agent.

38. The kit of claim 37, wherein the tonicity agent is selected from the group consisting of glycerin, lactose, mannitol, dextrose, sodium chloride, sodium sulfate and sorbitol.

39. The kit of claim 7, wherein the second vial further comprises a tonicity agent.

40. The kit of claim 39, wherein the tonicity agent is selected from the group consisting of glycerin, lactose, mannitol, dextrose, sodium chloride, sodium sulfate and sorbitol.

41. The kit of claim 7, wherein the first vial further comprises an antioxidant.

42. The kit of claim 41, wherein the antioxidant is selected from the group consisting of acetone sodium bisulfite, bisulfite sodium, butylated hydroxy anisole, butylated hydroxy toluene, cysteine, cysteinate HCl, dithionite sodium, gentisic acid, gentisic acid ethanolamine, glutamate monosodium, formaldehyde sulfoxylate sodium, metabisulfite potassium, metabisulfite sodium, monothioglycerol, propyl gallate, sulfite sodium, thioglycolate sodium, and ascorbic acid.

43. The kit of claim 7, wherein the second vial further comprises an antioxidant.

44. The kit of claim 43, wherein the antioxidant is selected from the group consisting of acetone sodium bisulfite, bisulfite sodium, butylated hydroxy anisole, butylated hydroxy toluene, cysteine, cysteinate HCl, dithionite sodium, gentisic acid, gentisic acid ethanolamine, glutamate monosodium, formaldehyde sulfoxylate sodium, metabisulfite potassium, metabisulfite sodium, monothioglycerol, propyl gallate, sulfite sodium, thioglycolate sodium, and ascorbic acid.

45. The kit of claim 7, wherein the first vial comprises:
anidulafungin, a stabilizing agent, a bulking agent, a solubilizing agent, and a buffer.

46. The kit of claim 45, wherein the first vial contains a solid formulation comprising 20 to 200 mg of anidulafungin and the second vial contains 10 to 60 milliliters of aqueous solution comprising about 10 to 30% w/v ethanol.

47. The kit of claim 7, wherein the first vial comprises:
anidulafungin, fructose, mannitol, polysorbate 80, and tartaric acid.

48. The kit of claim 47, wherein the first vial contains a solid formulation comprising 25 to 200 mg of anidulafungin and the second vial contains 10 to 60 milliliters of aqueous solution comprising about 10 to 30% w/v ethanol.

* * * * *